United States Patent [19]

Scheltinga et al.

[11] Patent Number: 5,203,344
[45] Date of Patent: Apr. 20, 1993

[54] METHOD AND APPARATUS FOR TAKING BIOELECTRICAL IMPEDANCE MEASUREMENTS USING PROXIMALLY POSITIONED ELECTRODES

[75] Inventors: Marc R. Scheltinga; Douglas W. Wilmore, both of Brookline, Mass.

[73] Assignee: Brigham and Women's Hospital, Boston, Mass.

[21] Appl. No.: 648,226

[22] Filed: Jan. 31, 1991

[51] Int. Cl.$^5$ .............................................. A61B 5/05
[52] U.S. Cl. .................................... 128/734; 128/693; 128/644
[58] Field of Search ............... 128/734, 639, 644, 774, 128/741, 693, 419 N, 802, 790, 795, 796

[56] References Cited

U.S. PATENT DOCUMENTS

| Re. 30,101 | 9/1979 | Kubicek et al. | 128/713 |
|---|---|---|---|
| 2,318,207 | 5/1943 | Ellis | 128/644 |
| 3,381,682 | 5/1968 | Figar | 128/2 S |
| 3,957,037 | 5/1976 | Fletcher et al. | 128/2.1 E |
| 3,971,365 | 7/1976 | Smith | 128/2.1 Z |
| 4,008,712 | 2/1977 | Nyboer | 128/2.1 Z |
| 4,016,868 | 4/1977 | Allison | 128/644 |
| 4,450,527 | 5/1984 | Sramek | 364/415 |
| 4,562,843 | 1/1986 | Djordjevich et al. | 128/672 |
| 4,649,932 | 3/1987 | Smith | 128/734 |
| 4,793,362 | 12/1988 | Tedner | 128/734 |
| 4,807,638 | 2/1989 | Scamek | 128/672 |
| 4,809,700 | 3/1989 | Castelli | 128/644 |
| 4,870,578 | 9/1989 | Vysin et al. | 364/413.05 |
| 4,880,014 | 11/1989 | Zarowitz et al. | 128/734 |
| 4,895,163 | 1/1990 | Libke et al. | 128/734 |
| 4,911,175 | 3/1990 | Shizgal | 128/734 |
| 4,947,862 | 8/1990 | Kelly | 128/734 |
| 4,949,727 | 8/1990 | Yamazaki et al. | 128/734 |

OTHER PUBLICATIONS

"Proximally Placed Electrodes Provide Impedance Values Which Predict Small Volume Blood Loss", M. Scheltinga et al., The Society of University Surgeons Residents' Program Abstracts, Section 80, p. 523, Feb. 10, 1990, Los Angeles, Calif.

"Whole Body and Regional Bioelectrical Impedance Analysis (BIA) Measurements During Critical Illness", M. Scheltinga and D. Wilmore Handout at ASPEN PG Course, 1991.

Primary Examiner—Max Hindenburg
Assistant Examiner—Guy V. Tucker
Attorney, Agent, or Firm—Basile and Hanlon

[57] ABSTRACT

First and second pairs of electrodes are connected to a bioelectrical impedance measuring device. The first pair of electrodes are then attached to a subject's body to introduce an electrical current in the subject's body. The second pair of electrodes are attached to the body in proximity with the elbow and the knee joint of the subject's body. The second pair of electrodes detect the impedance in the subject's body when the electrical current flows therein by the first pair of electrodes. The bioelectrical impedance measurement device measures the impedance detected by the second pair of electrodes.

7 Claims, 1 Drawing Sheet

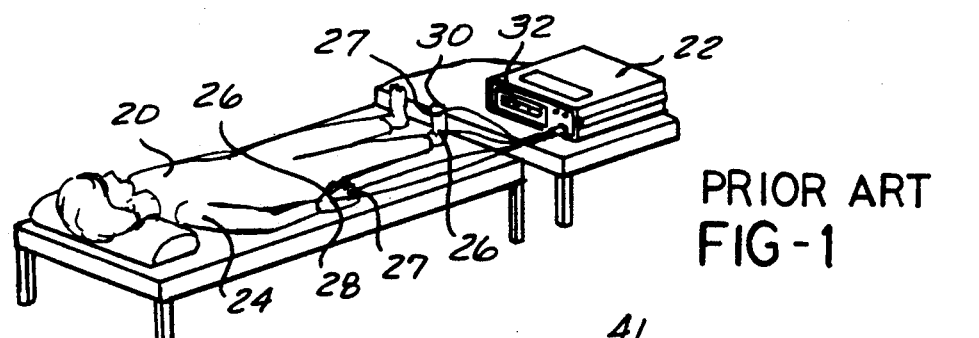
PRIOR ART
FIG-1
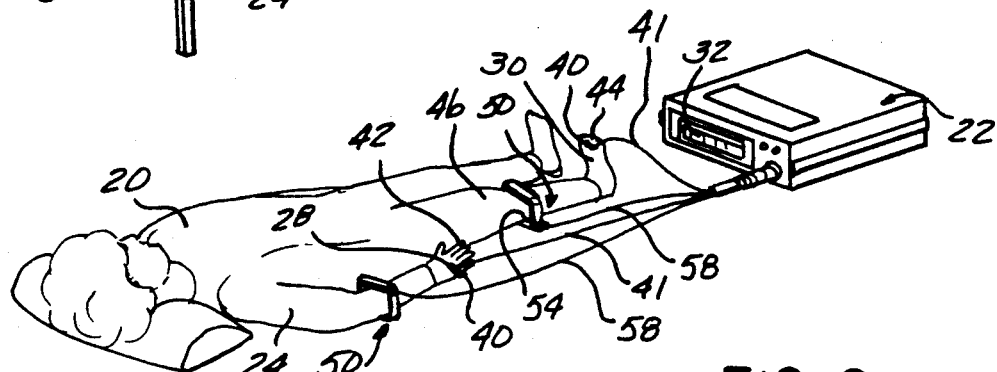
FIG-2
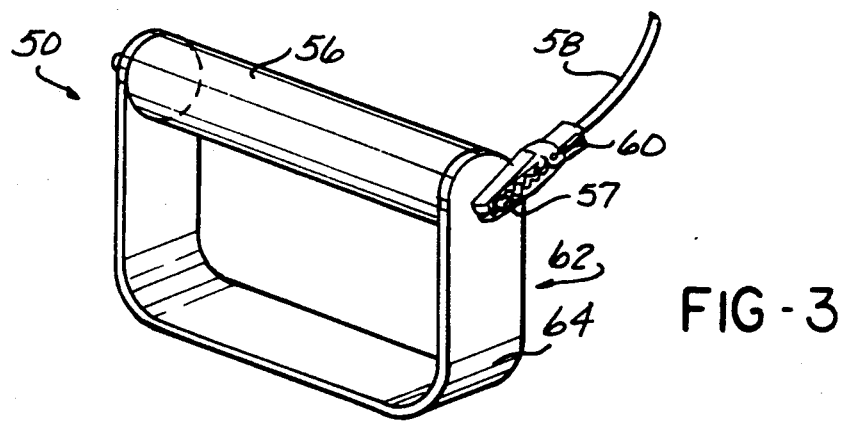
FIG-3
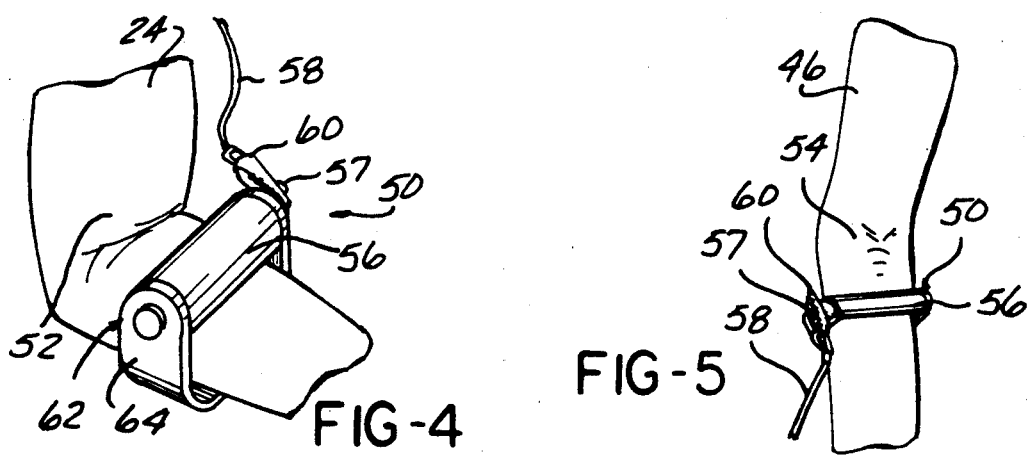
FIG-4
FIG-5

METHOD AND APPARATUS FOR TAKING BIOELECTRICAL IMPEDANCE MEASUREMENTS USING PROXIMALLY POSITIONED ELECTRODES

BACKGROUND OF THE INVENTION

1. Field of the Invention

This invention relates, in general, to bioelectrical impedance measurement apparatus and methods and, more specifically, to bioelectrical impedance measurement apparatus and methods using an impedance plethysmograph.

2. State of the Art

Bioelectrical impedance measurements have been employed to determine various body characteristics, such as blood flow, cardiac output and composition including an assessment of body fat, lean body mass and extracellular mass. To determine body composition, a four-electrode impedance plethysmograph is usually employed. A first pair of source or current electrodes is connected to a human body typically on a hand and a foot. Specifically, one source electrode is attached to the dorsal surface of a hand over the metacarpals, whereas the other source electrode is attached to the distal end of the third metatarsal bone. One electrode of a second pair of detecting or sensing electrodes is traditionally attached to the dorsal surface of a hand between the bony prominences of the wrist, whereas a second sensing electrode is positioned between the lateral and medial bony prominence of an ankle. An excitation current generated by the plethysmograph is applied to the source electrodes and thus introduced into the body. For example, an 800 microamphere, 50 kHz current is typically employed.

The human body opposes the conduction of electrical current and this ability to oppose current is called impedance. Impedance can be measured by the plethysmograph and analyzed into a resistance and reactance value. The whole body resistance is then combined in an equation with the weight and height of the subject to predict total body water (TBW). When TBW is predicted according to this technique, a reasonably high correlation is present with TBW volume determined from the "golden standard", namely, heavy water dilutional technique.

In the measurement technique described above, the arm, trunk and leg of the subject are connected in a serial fashion. However, the forearm and lower leg are body parts with small diameters in comparison to the upper arm, thigh and trunk. When the resistance is determined across individual parts of the human body, more than 50% of the whole body resistance signal is present in a forearm and a lower leg, although the contribution of these anatomical parts to body composition is less than 5%.

Thus, it would be desirable to provide a bioelectrical impedance measurement method and apparatus which increases the accuracy of a single body compositional measurement of a subject. It would also be desirable to provide a bioelectrical impedance measurement method and apparatus which provides body impedance measurements which are superior in their prediction of total body water (TBW) when compared to the conventional (whole body impedance) method. It would also be desirable to provide a bioelectrical impedance measurement method and apparatus which excludes the forearm and lower leg of a subject from the measurement so as to increase the accuracy of TBW prediction. Finally, it would be desirable to provide a bioelectrical impedance measurement method and apparatus which generates highly accurate body impedance measurements which may be used to improve fluid management of ill subjects in a clinical setting, such as in an intensive care unit.

SUMMARY OF THE INVENTION

The present invention is a method and apparatus for determining bioelectrical impedance measurements using electrodes positioned on proximal portions of body limbs.

The apparatus includes a bioelectrical impedance measuring device, such as an impedance plethysmograph, which generates a constant amplitude electrical current signal output of variable or high frequency. A first pair of electrodes connected by electrical leads to the plethysmograph is positioned on a hand and a foot of a subject's body. Activation of the plethysmograph causes an electrical current to flow through the first pair of electrodes.

A second pair of sensing electrodes, also connected to the plethysmograph, is respectively positioned in proximity with the elbow and knee joint of the subject and measures the impedance of the whole body minus the forearm and the lower leg.

By using this electrode position configuration, a measurement of impedance is obtained which includes the majority of the human body (i.e., ±95%), but which excludes high resistance body portions, such as the forearm and the lower leg. The impedance measurement obtained in this fashion will reflect TBW more accurately than traditional whole body measurements.

Preferably, each of the second pair of electrodes comprises a cylindrical, metal rod. Means for securely and removably attaching the rod to the subject's body are mounted on the rod. In a preferred embodiment, the attaching means comprises an elastic band. An electrical lead is attached to the rod at one end and to the bioelectrical impedance measuring device at the other end.

In the method of the present invention, the first pair of electrodes is attached to the hand and foot of the subject, respectively. Preferably, the first pair of electrodes is attached to the base of the third finger of one hand and the base of the third toe of one foot of the subject's body. The second pair of electrodes is then attached to the body in proximity with the elbow and the knee joint, respectively, of the subject.

The first and second pair of electrodes are then connected to a bioelectrical impedance measuring device, such as an impedance plethysmograph. The plethysmograph generates a constant amplitude electrical current signal of a variable or a high frequency which is introduced into the subject's body by the first pair of electrodes. The second pair of electrodes measures the impedance of the whole body minus the forearm and the lower leg.

The method and apparatus of the present invention provides body impedance measurements which are superior in their prediction of TBW when compared to traditional whole body impedance methods using distal positioned sensing electrodes. By using proximally positioned sensing or detecting electrodes, the impedance measurements bypass the forearm and the lower leg of the subject, which body parts provide greater than 50% of the total body resistance, but less than 5% of body composition. The method and apparatus of the present invention may also be employed to improve fluid management of ill subjects in a clinical setting, such as in an intensive care unit.

BRIEF DESCRIPTION OF THE DRAWING

The various features, advantages and other uses of the present invention will become more apparent by referring to the following detailed description and drawing in which:

FIG. 1 is a pictorial representation of a subject attached to an impedance plethysmograph according to a prior art method of electrode attachment;

FIG. 2 is a pictorial representation of a subject attached to an impedance plethysmograph according to the method and apparatus of the present invention;

FIG. 3 is a perspective view of one of the second pair of electrodes employed in the present invention;

FIG. 4 is a partial, perspective view showing the attachment of one of the second pair of electrodes adjacent the elbow of a subject; and FIG. 5 is a partial, pictorial representation showing the attachment of the other of the second pair of electrodes behind the knee joint of a subject.

DESCRIPTION OF THE PREFERRED EMBODIMENTS

Before describing the method and apparatus of the present invention in detail, a brief description of a conventional, prior art bioelectrical impedance measuring method will be presented.

FIG. 1 depicts a conventional prior art bioelectrical impedance measurement technique using an impedance plethysmograph having electrodes attached to distal portions of a subject's body. According to this conventional method, a subject 20 is typically disposed in a prone position with the arms 24 placed so that they do not touch the torso. First and second pairs of conductive spot electrodes 26 and 27 are connected by electrical leads to the terminals of the plethysmograph 22 and are positioned on the distal portions of one hand 28 and one foot 30, on either the right or left side, or either both on the same side, or on opposite sides of the subject's body.

An electrical current is generated by the plethysmograph 22 and passed through the first set of electrodes 27, while the other set of electrodes 26 detects the impedance of the subject's body therebetween. One of the electrodes 27 is attached by suitable means to the dorsal surface of the hand 28 over the metacarpals; while the other of the first pair of electrodes 27 is attached over the distal end of the third metatarsal bone in the foot 30. The second pair of electrodes 26 is attached to the dorsal surface of the hand 28 between the bony prominences of the wrist; while the other electrode 27 is attached to the foot 30 between the lateral and medial bony prominence of the ankle.

An excitation current, which is, for example, a current of 800 microampheres at 50 kHz, is introduced into the first pair electrodes 27 on the hand 28 and foot 30. The impedance of the subject's body is detected by the sensing electrodes 26 attached to the hand 28 and foot 30. The impedance measuring device 22 measures the whole body resistance and reactance and outputs such measured values to a visible display 32. These values are then combined with the subject's height and weight in an equation to calculate total body water, lean mass, fat-free mass, etc., as disclosed in detail in U.S. Pat. No. 4,911,175, the contents of which are incorporated herein by reference.

The unique features of the present invention are shown in general in FIG. 2 and in greater detail in FIGS. 3, 4 and 5. As shown in FIG. 2, the bioelectrical impedance measuring device 22 preferably comprises a four-electrode impedance plethysmograph such as one sold by RJL Systems, Inc., of Mt. Clemens, Michigan. As is conventionally known, such an impedance plethysmograph 22 includes a constant current source which generates a constant amplitude electrical current signal output. For example, the current signal output can be 800 microampheres at a constant 50 kHz. It should be noted that other frequencies may also be employed in the present invention as long as the impedance can still be accurately analyzed in separate vectors of resistance and reactance.

Further, the bioelectrical impedance measuring device 22 may also comprise a variable frequency current signal generator which outputs a plurality of variably selectible frequencies. Such variable frequencies may be advantageously employed, for example, to determine different components of body composition.

A first pair of source electrodes 40 is connected to the terminals of the plethysmograph 22 by electrical leads 41 and is positioned on the subject's body 20. The first pair of electrodes 40 may take any form, such as conventional spot electrodes. Preferably, the first pair of source electrodes 40 are respectively attached by means of a conductive gel to the surface of the skin near the base of the third finger 42 and the surface of the skin adjacent the base of the third toe 44 of the foot 30. A constant current signal output generated by the plethysmograph 22 will thus introduce a constant amplitude electrical current in the subject 20 through the first pair of electrodes 40. This current passes through the arm 24, torso, leg 46 and foot 30 of the subject 20.

A second pair of electrodes 50 is also connected to the bioelectrical impedance measuring device or plethysmograph 22 by electrical leads 58. In a preferred embodiment, the second pair of electrodes 50 is respectively attached to the subject 20 in proximity with the elbow 52 and in proximity with the knee joint 54. By way of example only, the second pair of electrodes 50 is located approximately one centimeter from the elbow 52 and one centimeter from the knee joint 54 on the bottom or top surface of the elbow 52 and the knee joint 54.

The second pair of electrodes 50 may take any suitable shape, such as convention spot electrodes described above. In a preferred embodiment, as shown in FIGS. 3-5, each of the second pair of electrodes 50 comprises a small diameter, conductive, metal, cylindrical rod 56. The rod 56 has a length of approximately 20 cm, for example. A short, smaller diameter extension or flange 57 extends integrally from one end of the rod 56. An electrical lead 58 connected at one end to the plethysmograph 22 is attached to the extension 57 by means of a suitable clip 60, such as a conventional alligator clip. Of course, other attachment means, such as solder, may also be employed to removably or fixedly connect the electrical lead 58 to the rod 56.

Each of the second pair of electrodes 50 also includes means for removably and securely attaching each of the second pair of electrodes 50 to the subject 20. The attaching means 62 preferably comprises an elastic band 64 which is secured at opposite ends to opposite ends of the rod 56. Alternately, two straps may be connected to opposite ends of the rod 56 and releasably joined together by a fastener, such as a VELCRO fastener.

According to the method of the present invention, the first pair of electrodes 40 is respectively attached to a hand 28 and a foot 30 of the subject 20, as described above. The opposite ends of each of the electrodes 40 are connected by electrical leads 41 to the bioelectrical impedance measuring device or plethysmograph 22. The second pair of electrodes 50 is then attached to the subject 20 in close proximity with the elbow 52 and the knee joint 54 of the subject 20. The leads 58 attached to the second pair of electrodes 50 are then connected to the plethysmograph 22.

Next, the plethysmograph 22 generates a constant amplitude electrical current signal. The first pair of electrodes 40 introduces the electrical current signal into the subject 20 such that the electrical current flows through the subject's body. The second pair of electrodes 50 detects the impedance in the subject's 20 body between the two electrodes 50. This impedance is measured by the plethysmograph 22 which provides the value of the impedance of the subject's 20 body between the second pair of electrodes 50.

This impedance value may be output on the display 32 on the plethysmograph 22 and then combined along with the subject's 20 height and weight in an equation to calculate total body mass or other body composition characteristics.

Various tests have been made to investigate the sensitivity of the present method in accurately predicting total body water.

EXAMPLE NO. 1

In this example, six studies were performed on three anesthetized, ventilated and stabilized dogs. Heavy water ($D_2O$) was used to measure total body water (TBW). After an equilibrium period, 10 cc normal saline/kg body weight was given as an intravenous fluid bolus to cause approximately a 2% increase of TBW. Impedance (Z) was measured at thirty minute intervals using pairs of proximally placed transdermal and surface electrodes in addition to "standard" distal paw surface electrodes, which correspond, respectively, to the method of the present invention and the attachment technique shown as prior art in FIG. 1 Impedance (Z) before infusion was calculated as the mean of three consecutive base line measurements; whereas the thirty minute post infusion impedance was used for Z "after". In the following table, impedance (Z) in ohms is shown as mean ±s.e.m.

TABLE NO. 1

|  | Proximal Transdermal | Proximal Surface | Distal Surface |
|---|---|---|---|
| Z "before" (n = 6) | 167 ± 5 | 176 ± 5 | 882 ± 61 |
| Z "after" (n = 6) | 163 ± 4* | 171 ± 5* | 871 ± 64 |

* = p < 0.001 compared to Z "before" by paired, 2-tailed t-test.

Proximal measurements detected a significant decrease in impedance after infusion; whereas changes registered by distal electrodes were not significant. In addition, TBW calculated ($TBW_{calc}$) using the formula: Z "after"×Bolus Volume/[Z "before" −Z "after"], was closely correlated ($R^2=0.98$) with TBW obtained using $D_2O$ ($TBW_{calc}=0.845 \times TBW_{D20}-2.415$).

Thus, the change in volume resulting from the saline infusion was accurately detected by the proximally positioned electrodes. This infusion was not detected by conventional distal mounted electrodes. In addition, proximal resistance values obtained over sixty minutes preceding this saline infusion demonstrated less variation compared to traditionally measured distal resistance values.

EXAMPLE NO. 2

Impedance (Z) was measured in ten healthy donors five minutes before and immediately after blood donation using electrodes placed on the proximal forearm and lower leg in addition to standard distal electrode placement as shown in FIG. 1. Eight healthy volunteers underwent the same measurements without donating blood and served as controls. TBW was predicted using nomograms based on height and weight. In Table No. 2, Z (in ohms) is shown as means ±s.e.m.

TABLE NO. 2

|  | PROXIMAL | | | DISTAL | | |
|---|---|---|---|---|---|---|
|  | $Z_{before}$ | $Z_{after}$ | $\Delta Z_{proximal}(\%)$ | $Z_{before}$ | $Z_{after}$ | $\Delta Z_{distal}$ |
| Controls (n = 8) | 255 ± 13 | 256 ± 13 | 0.2 ± 0.5 | 516 ± 23 | 523 ± 23* | 1.3 ± 0.4 |
| Donors (n = 10) | 251 ± 10 | 255 ± 11* | 1.3 ± 0.5 | 514 ± 18 | 521 ± 19** | 1.5 ± 0.3 |

*p < 0.02,
**p < 0.01 compared to $Z_{before}$ by paired, 2-tailed test.

Proximal positioned electrodes detected a significant change in Z in the Donor-group but not in the Control-group; whereas distally placed electrodes detected significant $\Delta Z$ in both groups. Increased $Z_{distal}$ could be due to ongoing fluid redistribution in the limbs secondary to the effects of Changing from standing to a supine position. TBW predicted from nomograms correlated better with $Z_{proximal}$ (TBW (ltr)=75−0.152×$Z_{proximal}$, r=0.86, p<0.001) than with $Z_{distal}$ (TBW (ltr)=77−0.079×$Z_{distal}$, r=0.78, p<0.001). The mean loss of TBW predicted from $\Delta Z_{proximal}$ using the regression formula was 517 ml, whereas the mean volume of domated blood measured by weight was 509 ml.

In this example, the proximally placed electrodes in accordance with the present invention accurately detected a 2% decrease in conducting volume associated with blood donation, whereas standard distal placed electrodes did not. In addition, proximal impedance values correlated better with TBW obtained from nomograms than did distal impedance values.

In summary, there has been disclosed a unique method and apparatus for taking bioelectrical impedance measurements which uniquely uses proximally positioned electrodes. This method and apparatus provides more accurate impedance measurements which correlate better with standard nomogram TBW predicted values. The method and apparatus is easy to employ using conventional bioelectrical impedance measuring devices, such as impedance plethysmographs.

What is claimed is:

1. A method for measuring bioelectrical impedance of a subject's body comprising the steps of:
    attaching first and second electrodes to one hand and one foot of the subject's body, respectively;

attaching third and fourth electrodes to the body of the subject in proximity with the elbow and the knee joint of the subject's body, respectivley, the third electrode positioned about one centimeter from the elbow of the subject, the fourth electrode positioned about one centimeter from the knee joint of the subject;

electrically connecting the first, second, third and fourth electrodes to a bioelectrical impedance measuring device;

generating an electrical current signal from the bioelectrical impedance measuring device;

introducing the electrical signal into the subject's body by the first and second electrodes; and measuring the impedance in the subject's body between the third and fourth electrodes by the bioelectrical impedance measuring device.

2. The method of claim 1 wherein the bioelectrical impedance measuring device is an impedance plethysmograph.

3. A method for measuring bioelectrical impedance of a subject's body comprising the steps of:

attaching first and second electrodes to one hand and one foot of the subject's body, respectively;

attaching third and fourth electrodes to the body of the subject in proximity with the elbow and the knee joint of the subject's body, respectively, the third and fourth electrodes each comprising:
  a cylindrical metal rod;
  means for securely attaching the rod to the subject's body; and
  means for attaching an electrical lead to the rod, the electrical lead also being connected to a bioelectrical impedance measuring device;

electrically connecting the first, second, third and fourth electrodes to a bioelectrical impedance measuring device;

generating an electrical current signal from the bioelectrical impedance measuring device;

introducing the electrical signal into the subject's body by the first and second electrodes; and measuring the impedance in the subject's body between the third and fourth electrodes by the bioelectrical impedance measuring device.

4. The method of claim 3 wherein the bioelectrical impedance measuring device is an impedance plethysmograph.

5. A bioelectrical apparatus for measuring impedance of the subject's body, comprising:

a bioelectrical impedance measuring device which generates an electrical current signal output;

first and second electrodes connected to the bioelectrical impedance measuring device and adapted to be attached to the subject's body for introducing the electrical current signal into the subject's body; and third and fourth electrodes respectively adapted to be attached to the subject's body in proximity with the elbow and the knee joint of the subject's body, respectively, and electrically connected to the bioelectrical impedance measuring device for detecting the impedance of the subject's body between the third and fourth electrodes, the third and fourth electrodes each comprising:
  a cylindrical metal rod;
  means for securely attaching the rod to the subject's body; and
  means for attaching an electrical lead to the rod, the electrical lead also being connected to the bioelectrical impedance measuring device.

6. The apparatus of claim 5 wherein the bioelectrical impedance measuring device is an impedance plethysmograph.

7. The apparatus of claim 5 wherein:
the means for attaching the electrical lead to the rod comprises means for releasably attaching the electrical lead to the rod.

* * * * *